(12) United States Patent
Coatoam

(10) Patent No.: US 7,341,453 B2
(45) Date of Patent: Mar. 11, 2008

(54) DENTAL IMPLANT METHOD AND APPARATUS

(76) Inventor: Gary W. Coatoam, 3122 Tala Loop, Longwood, FL (US) 32779

( * ) Notice: Subject to any disclaimer, the term of this patent is extended or adjusted under 35 U.S.C. 154(b) by 410 days.

(21) Appl. No.: 10/874,135

(22) Filed: Jun. 22, 2004

(65) Prior Publication Data

US 2004/0265781 A1  Dec. 30, 2004

Related U.S. Application Data

(62) Division of application No. 10/286,490, filed on Nov. 1, 2002, now abandoned.

(51) Int. Cl.
*A61C 8/00* (2006.01)
(52) U.S. Cl. ...................................... 433/173
(58) Field of Classification Search ................ 433/172, 433/173, 174, 175, 176, 165, 166
See application file for complete search history.

(56) References Cited

U.S. PATENT DOCUMENTS

| | | |
|---|---|---|
| 3,589,011 A | 6/1971 | Sneer |
| 3,672,058 A | 6/1972 | Nikoghossian |
| 3,797,113 A | 3/1974 | Brainin |
| 3,979,828 A | 9/1976 | Taylor |
| 4,016,651 A | 4/1977 | Kawahara et al. |
| 4,324,550 A | 4/1982 | Reuther et al. |
| 4,416,629 A | 11/1983 | Mozsary et al. |
| 4,713,003 A | 12/1987 | Symington et al. |
| 5,246,370 A * | 9/1993 | Coatoam ................ 433/173 |
| 5,310,343 A | 5/1994 | Hasegawa et al. |
| 5,591,029 A | 1/1997 | Zuest |
| 5,885,079 A | 3/1999 | Niznick |
| 5,919,043 A | 7/1999 | Weigl |
| 6,012,923 A | 1/2000 | Bassett et al. |
| 6,174,167 B1 | 1/2001 | Wohrle |
| 6,217,333 B1 | 4/2001 | Ercoli |
| 6,283,754 B1 | 9/2001 | Wohrle |
| 6,527,554 B2 | 3/2003 | Hurson et al. |
| 6,854,972 B1 * | 2/2005 | Elian .................... 433/173 |
| 2002/0168614 A1 | 11/2002 | Riley |

* cited by examiner

*Primary Examiner*—Melba Bumgarner
(74) *Attorney, Agent, or Firm*—Allen, Dyer, Doppelt, Milbrath & Gilchrist, P.A.

(57) ABSTRACT

A dental implant (105,137,156) has an elongated body (100) having first and second end portions (101,103) and having a root on one end portion (104,115,116) for attaching to a patient's jawbone to replace the root of a removed tooth. The root portion (104,115,116) has an anatomically shaped portion between the end portions of the body for fitting into a jawbone opening below the gum tissue of a patient when the root (104,115,116) is attached to a jawbone. An artificial tooth abutment (103,112 & 113) is formed on the other end of the elongated body for attaching an artificial tooth thereon of the abutment extending above the gum line of a patient. A method of attaching a dental implant (105,137,156) includes the steps of extracting a patient's tooth and selecting the dental implant (105,137,156) of the apparatus and attaching the dental implant root (104,115,116) with the jawbone of a patient with the abutment (103,112,113) extending above the gum tissue of the patient and attaching the artificial tooth to the abutment.

13 Claims, 3 Drawing Sheets

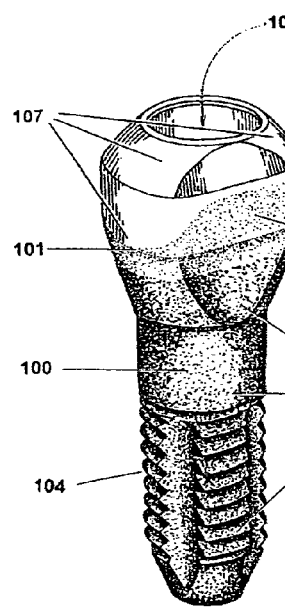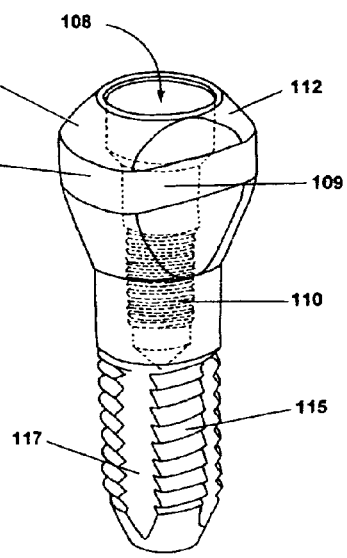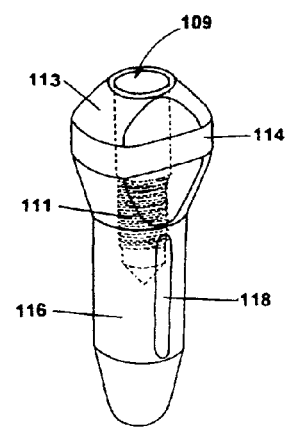
FIG. 1   FIG. 2   FIG. 3
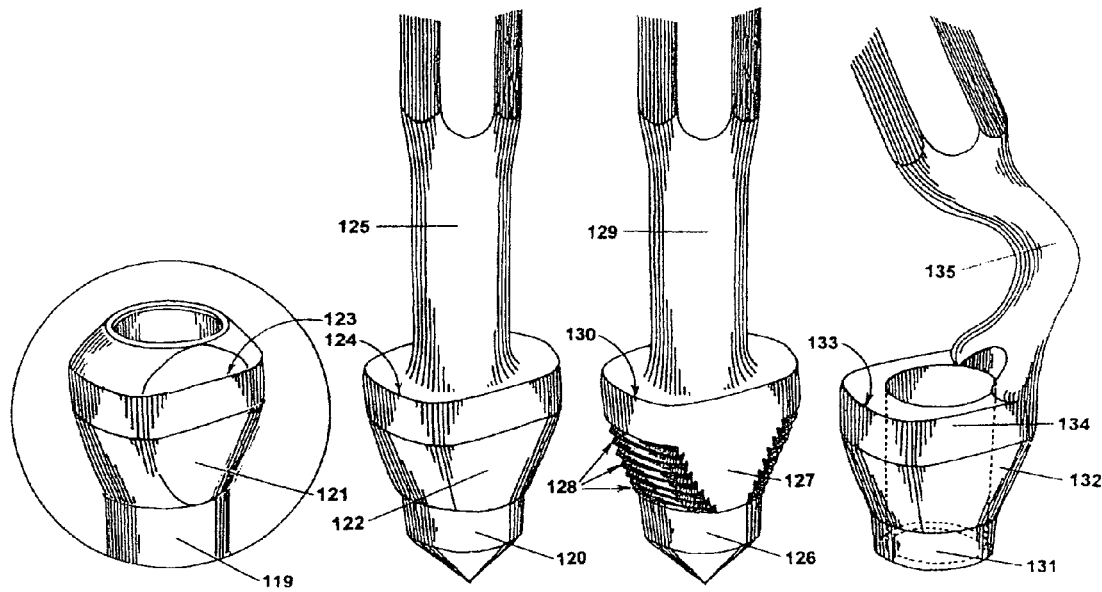
FIG. 4   FIG. 5   FIG. 6   FIG. 7

DENTAL IMPLANT METHOD AND APPARATUS

This is a division of patent application Ser. No. 10/286,490, filed Nov. 1, 2002 now abandoned for a Dental Implant Method and Apparatus.

BACKGROUND OF THE INVENTION

1. Field of the Invention

The present invention relates generally to the field of dental implants and in particular to a system of anatomic dental implants, which may be converted to an anatomic facsimile of a natural tooth. The present invention also relates to eliminating the quandary of having to decide if the implant/abutment seam will compromise aesthetics or if the implant/abutment seam will compromise the integrity and long-term of the bone. The present invention also relates to ancillary components and instruments related to the placement and restoration of the anatomic implant.

2. Background of the Invention

A dental implant is an artificial tooth made of metal with a porcelain coating designed to make it look real. Its most important component is its root, a titanium anchor that is surgically implanted into the jawbone, usually by an oral surgeon or periodontal surgeon. Generally, the anchor is implanted alone, without the tooth. Gradually, during a healing period the bone grows around the implant securing it in place. An abutment is added to the implant for the artificial tooth to sit upon and then a replacement tooth or crown is attached to the metal post. Implants can also be used to anchor bridges and permanent dentures when more than one tooth is missing.

The replacement of a patient's tooth or placement of an anchorage fixture for attaching an overlying fixed or removal prosthesis initially consists of the placement of endosseous anchorage implants to which subsequent attachments might be added. Systems as described by U.S. Pat. No. 3,589,011 to Sneer, U.S. Pat. No. 3,797,113 to Brainin, U.S. Pat. No. 3,979,828 to Taylor, U.S. Pat. No. 4,324,550 to Reuther et al., and U.S. Pat. No. 4,416,679 to Mozsary et al., have proven to be successful for the long term anchorage of the endosseous dental implants to the maxillary and mandibular jawbones.

The placement of endosseous dental implants has evolved using 2 surgical approaches. One of these approaches uses a submerged technique where the implant is placed at or below the crest of the bone. The gingiva is closed over the bone and the implant thereby submerging the implant. The other surgical approach involves placement of an implant that extends coronally beyond the alveolar crest where the soft tissue flap is placed around a cover screw extending from the implant body. Once the dental implant has become permanently affixed to the bone by means of the process known as osseointegration, abutment attachments are added to the implant in order to make it suitable for the placement of a prosthetic tooth crown. Those prosthetic teeth crowns are then generally affixed to the abutments by means of fixation screws or by means of permanent cementation. Because the abutment is added to the implant, there is a seam (microgap) between the implant and the abutment. Additionally most implants are manufactured with a polished or smooth machined collar combined with a rough implant body. Studies have shown that the seam (microgap) and the junction of the rough surface and the smooth collar (r/s border) cause crestal bone resorption when placed in close approximation to the crestal bone. Ercoli, U.S. Pat. No. 6,217,333, attempted to address this issue by creating a curved top on the implant so that the seam and the r/s border more closely approximated the saddle-shaped crestal bone. This innovation only partially addressed the issue because the seam (microgap) persisted, though in an altered form; also Ercoli 333 presumed that finite shapes could accommodate the infinite variety of crestal bone shapes. Similarly, Wöhrle, U.S. Pat. Nos. 6,174,167 and 6,283,754 created an implant with a scalloped coating that was designed to remain below, yet follow the crest of bone. Above this scalloped coating there was intended to be a different treatment of the implant surface, such as a machined collar, that was distinctly compatible with the soft tissue. This concept of scalloped exclusion of the collar surface from the subosseous regions because the collar is only compatible with the gum tissue is not in keeping with the technology of the PACE implant, as marketed by Coatoam since 1996 where the surface treatment of the collar is compatible to both bone and tissue attachment. This collar transition does not require a scalloped design because the collar treatment can go below the crest of bone or be above the crest of bone without creating any bone die-back. Additionally there is good gingival attachment to this surface. Also the PACE implant has been marketed since 1996 as being adjustable by the doctor so that the top edge can be scalloped like the pre-fabricated Ercoli 333 design. This ability to adjust the implant provides the property of keeping the treated collar in a subgingival position where it would not retain plaque, plus the property of being able to adjust the implant edge allows for adaptation of the implant when it is surgically placed in the patient's mouth. This is particularly valuable in maxillary anterior teeth where the crest of bone most often is not actually symmetrically scalloped, but rather is much higher on the facial aspect than it is on the interproximal or palatal aspects of the tooth socket. Both Ercoli 333 and Wöhrle 167 & 754 have symmetrical designs, and the implant edge in Ercoli 333 along with the collar in Wöhrle 167 & 754 can end up in a subosseous position on the palatal aspect when the implants are placed in the maxillary anterior area thereby leading to potential bone die-back in these regions.

Because implant abutments are subject to rotational loosening, the dental prosthesis, which is subsequently affixed to the post attachments, is also subject to this unscrewing phenomenon. This can lead to loosening and failure of the dental prosthesis. In order to prevent this phenomenon most implant systems add a non-round interconnection or a Morse taper between the endosseous dental implant and the abutment to prevent rotational movement. In most designs, a screw is then passed through the abutment, affixing it to the body of the implant. This screw generally has a positive seat in some portion of the abutment. Once the screw is tightened with sufficient torque, the abutment is firmly anchored to the dental implant. The coronal extent of the abutment usually has some design feature such as a flat side that ultimately engages the crown prosthesis to provide a non-rotational feature to the cemented crown. In U.S. Pat. No. Des. 401,695 Daftary described a non-round anatomic shape that prevents crown rotation. Rotational forces to the abutment are absorbed at the implant by the non-round component rather than being transmitted directly to the screw itself. These non-round components are generally shaped like a hex, an octagon, a multi-pointed star, or a spline. In each case the seam between the implant and the abutment presents a problem after surgical implant placement because of subsequent bone dieback.

Another type of anti-rotational feature on implants is the non-round anatomically shaped implant. This type of implant was described in U.S. Pat. No. 5,246,370 to Coatoam. In this type of system the crown attaches directly down onto the non-round implant body. Since the edge of the head of the implant is a machined non-round anatomical shape the crown cannot rotate. In these systems the anti-rotational feature is the non-round implant shape of the exit profile. With this type of design it is necessary to set the timing of the implant so that the anatomic shape corresponds to the replaced tooth. It is also necessary to keep the edge of the implant in a position above the crest of bone because even though the crown margin finishes on the implant body, that margin may also act as a microgap that can lead to bone loss. In the application of the Coatoam patent 370, the commercially available PACE implant can be altered so that the bevel at the top edge of the implant can be altered by the doctor to accommodate the infinite variety of shapes of the crestal bone. However, whenever the implant was altered it then became essential for the restorative doctor to take direct impressions of the altered dental implant rather than using available impression transfer posts and implant analogs. In U.S. Pat. No. 5,759,034 Daftary proposed a non-round anatomically shaped implant similar to the 370 Coatoam implant but in 034 Daftary there is still an implant/abutment seam between the crest of bone and the margin of the crown.

There exists a need for an anatomically shaped dental implant that can be placed so that the crestal bone does not die back as a consequence of an implant/abutment seam. Also there is a need to eliminate this potentially weak implant/abutment seam so that smaller implants can be manufactured without having to enlarge the abutment in order to accommodate anti-rotational components and connectors to the implant. Further, there is a need for an anatomically shaped implant where the edge of the margin of the final crown can be variably and infinitely set by the doctor and the laboratory technician as ultimately determined by the shape of the adjacent crestal bone and the junctional gingival epithelium.

SUMMARY OF THE INVENTION

The present invention provides a method and a system for placing dental implants in the alveolus of the maxillary or mandibular jawbones. The implant has a distal insertion end that may be rod shaped, screw shaped and/or have fins to assist in retention in the bony alveolus. The implant may be made of biocompatible materials including but not limited to metal, ceramic, glasses or any combination thereof, and potentially having various surface coatings of materials such as titanium beads, titanium plasma spray, hydroxylapatite, or bone growth chemicals or similar coatings to enhance attachment to the bone. The distal end of the implant is inserted into the bone by preparing a hole for the implant. That hole may be made by extraction of a tooth, or a drilled hole in the bone, or a hole made by driving chisels or osteotomes into the bone, and/or alterations of the hole made by round or non-round osteotome devices, drills or chisels. The implants may have a typical rod shape along the entire length, or the implants may have an enlarged anatomically shaped non-round head. The anatomically shaped implants may be inserted partially or fully into extraction sites, or into holes that have had the top portion of the osteotomy site altered and enlarged by free-hand means and associated devices. Such associated devices may be counter-bevel drills, non-round osteotomes, non-round rasps, round rasps, chisels, drill guides or drilling jigs. In some instances the various implants may be inserted into the prepared hole by compression fit. In other instances the implants may be screwed into the bone or affixed by fixed or retractable fins. Bone graft materials, bone growth enhancement chemicals, barrier membranes and/or grids or meshes may be used to enhance bone attachment or build bone around the implants.

The proximal end of the implant extends out of the prepared hole in the bone. The proximal ends of the implants have gently rounded, convex amalgamated anatomical abutment bases. The amalgamated abutment base may be partially coated with gold, porcelain, gold-colored titanium nitrite or other substances used to improve aesthetics. The amalgamated abutment may have a bored hole to accommodate various extenders. This bored hole may be non-round, but the actual anatomical shape of the abutment base or Morse taper of the round abutment provides the essential anti-rotational component to the implant. For that reason the shape of this tube-like extension is not critical since any non-round design of this opening may be a redundancy in regard to anti-rotational design. This would also be true of non-round proximal extensions of the abutment base such as hexes, slots, or splines, which might be thought to alter this invention, but would not enhance the design. It is also nonessential that any abutment extender has an indexed shape to prevent crown rotation. The crown is prevented from rotating by direct attachment to the anatomically shaped implant/abutment head.

At the bottom of the bore opening there is a threaded extension of the bored opening. This threaded extension can receive a threadedly inserted screw or non-threadedly inserted rod extension. The proximal end can accommodate various fittings that act as posts for a crown and post design or for post and core extenders that will provide added retention to subsequent dental crown prosthesis. This feature facilitates the placement of angled post and core extenders and anatomic coping attachments that are in keeping with dental technology that has been used to restore natural teeth for many years. The doctors' familiarity with these common dental techniques is a meaningful strength of this system.

In keeping with the traditional dental procedures of placement of post and core inserts into natural teeth, it is desirable but not essential that the margin of the core portion at the implant body be contained within the confines of the crown itself. However, unlike natural teeth, implants are not subject to decay, so if some portion of the post and core seam extends below the crown margin this would not be an adverse feature unless that core/implant margin extended too close to the crest of bone.

BRIEF DESCRIPTION OF THE DRAWING

FIG. 1 is a representative perspective view of an anatomically shaped dental implant with an amalgamated abutment base.

FIG. 2 is a cross-sectional view of FIG. 1.

FIG. 3 is a cross-sectional, perspective view of one of the possible variations of the implant depicted in FIG. 2.

FIG. 4 is a perspective view of the head of an implant in accordance with the present invention.

FIGS. 5, 6, 7 are perspective views of various dental instruments that generally relate to the shape of the dental implant in FIG. 4.

DETAILED DESCRIPTION OF THE PREFERRED EMBODIMENTS

Figures 8, 9, 10:
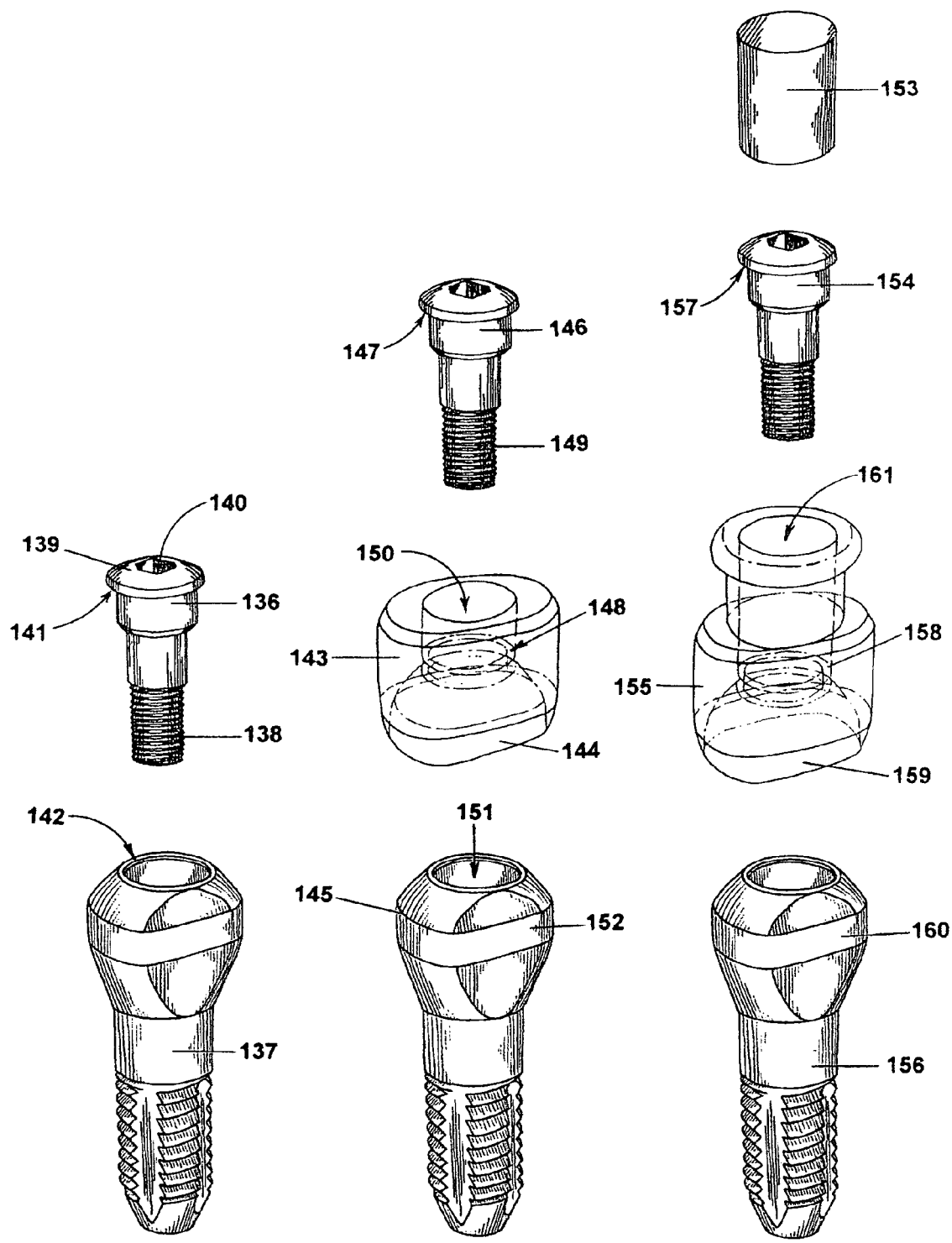
FIG. 8 is an exploded perspective view of stacked components showing a surgical cover screw and an implant in accordance with the present invention.
FIG. 9 is an exploded perspective view of stacked components showing a hold-down screw, healing cap, and an implant.
FIG. 10 is an exploded perspective view of stacked components showing a plug, a hold-down screw, an impression transfer post, and an implant.

Referring to the drawings, and particularly FIG. 1, a dental implant with a cylindrical body 100, and an anatomically shaped proximal end 101, has nearly parallel walls 102, and has an integrated anatomically shaped abutment base 103 formed as part of the implant and not a separate attachment. Transitional nearly parallel walls 102 between the abutment and the implant adjoin the abutment base to the implant. These walls may have a slight convergence in the coronal direction to facilitate draw of the prosthetic component. This entire assembly is preferably made from titanium or an alloy thereof, and may be cut from one piece of stock material. If the implant body is made of a different material than that of the integrated abutment, the two pieces are permanently fused without any microgap being present after fusion of the parts. This integrated or amalgamated abutment eliminates any abutment/implant seam below the bone or gum tissue. The seam has been implicated in bone die back, so elimination of the seam maximizes health around the implant. The margins of the crown, which will be fabricated in the laboratory will generally finish somewhere on the nearly parallel walls 102. These parallel walls allow the restorative doctor to variably alter the depth of the margins of the crown relative to the vertical position of the implant within the bone and gum tissue. Owing to the bulk of metal on the facial wall, the doctor may elect to alter the implant with a dental drill and bur to accept a greater bulk of crown material. This places the crown margin in the most ideal subgingival position for aesthetics while assuring that the hermetically sealed crown margin is high enough above the crest of bone to reduce the potential for any bone die back. The implant may have various grooves, threads and/or fins 104. The implant and portions of the parallel walls may have various coatings such as titanium plasma spray, acid etching, grit blast, hydroxylapatite, ceramics or biological coatings 105 or a combination thereof. The parallel walls, which comprise the collar of the implant may have a various coatings or surface treatments 106 that are different from those on the implant body 105. The anatomical abutment base 103 and a portion of the parallel walls 102 may be coated with gold, titanium nitride, or ceramics 107. The top of the amalgamated abutment/implant may have a cylindrical opening 108 to receive various castable or threaded post inserts Referring to FIGS. 2 and 3, the anatomical shape of the proximal end of the implant may be ovoid, triangular, rectangular, or circular, in keeping with the general shape of natural teeth. In referring back to the standard view of the implant FIG. 1 there is a cylindrical opening 108, which also can be seen in the cross-sectional view of the implant FIG. 2. In comparing FIG. 2 to FIG. 3 it may be noted that the cylindrical openings 108 and 109 in the two implants may vary in diameter relative to the size of the implants. The cylindrical opening may also step down in diameter 109 as it goes more deeply into the implant. In both sizes of implants there is a threaded opening 110 in FIGS. 2 and 111 in FIG. 3 at the distal end of the tube-like opening. In various sizes and shapes of the anatomic implants there are convex and anatomically shaped proximal ends 112 in FIGS. 2 and 113 in FIG. 3 with proportionately sized seamless nearly parallel walls 102 in FIGS. 2 and 114 in FIG. 3. The implants may have threads 115 in FIG. 2 or cylindrical side 116 in FIG. 3, and may have vertical grooves 117 and 118 or concentric grooved rings.

FIG. 4 is a perspective view of a certain sized dental implant. FIGS. 5, 6, and 7, are proportionately sized dental instruments that can be used to place that implant. Though these instruments are not absolutely essential for implant placement, they are helpful in sizing the osteotomy site, selecting the proper sized implant, and assuring proper depth of insertion of the dental implant. Where the implant has a distal shaft 119 of a determined diameter, each of the instruments has a distal shaft 120, which is just microns smaller in diameter to prevent binding of the instrument in the prepared osteotomy hole. The smooth osteotome FIG. 5 has a body shape 122 identical in size and dimension to the head of the implant 121 of FIG. 4. This smooth anatomic osteotome can be placed in an extraction site or in a prepared osteotomy site to determine the relationship of the implant to the site. In an extraction site for instance, it is desirous for the top edge of the parallel walls of the implant 123 to remain above the crest of bone. If the smooth anatomical osteotome FIG. 5 is inserted into the extraction site or the prepared site, and the top edge 124 goes below the crest of bone, a larger implant is generally indicated or bone grafting may be necessary. If the top edge 124 is too coronal to the crest of bone, a smaller implant may be desired. It is also possible to reshape the coronal portion of the osteotomy site to set the top edge 124 a little more in an apical direction by applying a gentle blow with a mallet to the end of the instrument shaft 125. This shaft 125 may be straight or contra-angled. When the osteotomy site is a free-hand creation, or in cases where it might be desirous to increase the anatomical opening of an extraction site, the anatomical rasp FIG. 6 may be used. As with the smooth anatomical osteotome FIG. 5, the anatomical rasp FIG. 6 has a slightly smaller distal bore 126 than the shaft of the dental implant 117. However, the anatomical rasp has a body shape 127 that is identical in size and shape to the implant body shape 121, just like the anatomical osteotome 122. The distinguishing feature between the anatomical osteotome and the anatomical rasp are ridges 128 that act like cutting teeth when a mallet blow is delivered to the end of the instrument handle 129. This handle 129 may also be contra-angled. The anatomical rasp FIG. 6 functions as a bone file to alter the most coronal opening of the osteotomy site. This rasp also has a demarcation edge 130 that corresponds to the top edge of the parallel walls of the implant 123. This top edge 130 is used as a reference point as the osteotomy site is shaped to receive the implant by repeated blows to the instrument handle 129.

The final shaping of the coronal portion of the osteotomy site might be formed by reinsertion of the anatomic osteotome. FIG. 5. A drill guide FIG. 7 may also be used. The drill guide FIG. 7, is similar to the drill guide described in my prior U.S. Pat. No. 5,246,370. This drill guide has a distal bore 131, and a body shape 132 and a demarcation edge 133 like the other instruments. However, it also has a through bore 134 to accommodate drills, plus it has a multi-angled handle 135 for easier positioning in osteotomy or extraction sites.

Referring to FIG. 8, there is a surgical setscrew 136 that is threadedly attached to the implant 137 by means of threads 138 at the end of the component. There is a low profile screw head 139 with a hex hole 140, or slot into which an engagement wrench or screwdriver is inserted. This surgical setscrew has a lip 141 that hermetically seals the top edge of the opening of the implant 142 during any healing phase. Though the implant is anatomically shaped, the components used to seal the implant during surgical healing can be standard cylindrical shapes that can achieve a tight, fluid-free seal.

FIG. 9 depicts an anatomically shaped healing cap 143 that is made of a plastic material such as methyl methacrylate or Delron. This healing cap is generally placed on the implant after a period of time that is sufficient to assume that the implant is either integrated or affixed to the bone in a stable fashion. The healing cap has a flange 144 that engages the top ring of the implant 145, and is threadedly attached to the implant by means of a hold-down screw 146. This hold-down screw 146 may be similar or identical in design to the surgical setscrew 136. The hold-down screw has a lip 147 that engages a shoulder 148 in the anatomically shaped healing cap. The threads 149 of the hold down screw pass through the central opening 150 of the healing cap and are threadedly inserted into the implant 151. As the screw is tightened, the flange 144 of the anatomically shaped healing cap slides down the parallel walls 152 of the implant, thereby retracting the gingiva. Since the anatomic healing cap is made of plastic, the flange 144 can be easily adjusted by means of grinding with an acrylic burr if the flange impinges on attached gingival tissue or bone when the healing cap is threadedly seated onto the implant by means of the hold down screw 146.

In examining FIG. 9, there is a bulk of material at the nearly parallel facial wall 145 of the implant. It is possible for the restorative doctor to alter this facial wall if a greater depth of porcelain is desired in this area when the final crown is fabricated. If any alteration is performed, then a direct impression will be taken of the altered implant in the patient's mouth so that this alteration can be duplicated on a laboratory model that is poured up from the direct impression.

In referring to FIG. 10, there is a silicone plug 153, a hold-down screw 154, an anatomically shaped impression transfer post 155, and an implant 156. The hold down screw 154 serves a similar purpose to the hold down screw 146 in FIG. 9. This hold down screw also has a lip 157, which engages a shoulder 158 in the impression transfer post 155. The plastic impression transfer post has a flange 159, which engages the parallel walls 160 of the implant 156. This flange 159 can be adjusted with a burr if it extends too far under the gum tissue thereby impinging on the junctional epithelial attachment or on the bone. After any necessary adjustment is made to the flange of the impression transfer post, it is held tight to the implant by the hold down screw, which is threadedly attached to the implant. The silicone plug 153 may then be inserted into the hole 161 of the impression transfer post so that dental impression material will not flow down into the hole. The doctor then takes an impression. Once the impression is set it is removed from the mouth. The impression transfer post 155 with the silicone plug 153, and hold down screw 154 are removed from the implant in the patient's mouth. This impression post apparatus is then threadedly inserted into a facsimile of the implant called an implant analog. This combination of impression transfer post and implant analog is then seated into the impression that was taken of the patient's mouth. The impression is then poured up using dental stone. Once the poured up impression is set, the impression transfer post is removed from the implant analog. Because the flange extended under the gum tissue, the removal of this component from the impression results in clear access to the parallel walls of the implant analog. It is along these nearly parallel walls that the margin of the crown will be established. The nearly parallel walls provide flexibility in establishing the position of the crown margin.

Figures 11, 12, 13:
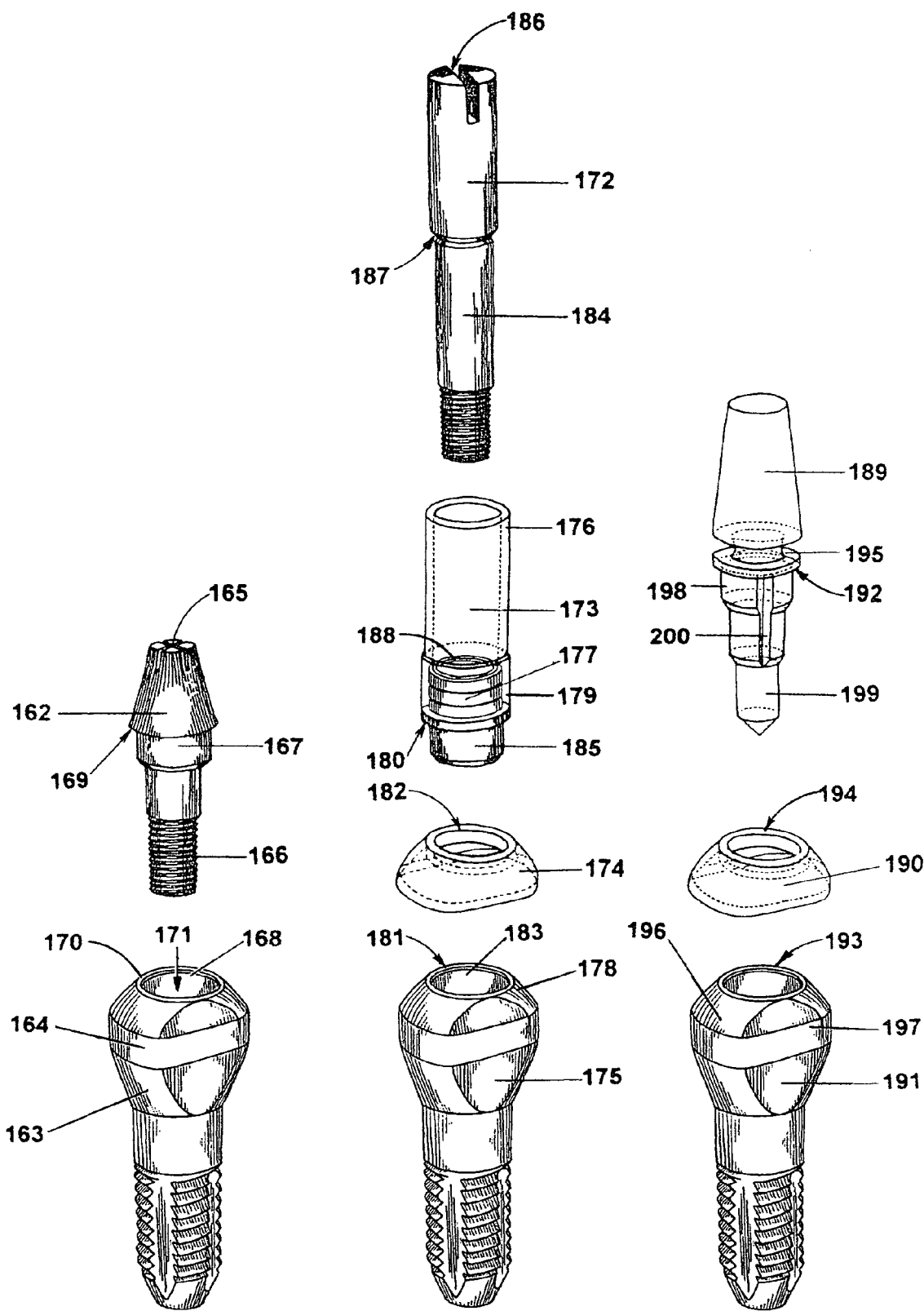
FIG. 11 is a representative perspective view of stacked components showing a straight screw-in post and core extender and an implant.
FIG. 12 is a representative perspective view of stacked components showing a prosthetic screw, an extension cast-on, an indexing sleeve and an implant.
FIG. 13 is a representative perspective view of stacked components showing a castable post and core, an indexing sleeve and an implant.

FIG. 11 depicts an abutment extender 162, as it would be inserted into an implant 163. Though the Ferrell effect of retention of the crown is primarily accomplished by placement of the crown margin on the parallel walls 164 of the implant/abutment, there are times when the doctor may desire additional crown retention. The abutment extender 162 may be used for this purpose. This extender has a wrench or screwdriver engagement feature 164, which is used to threadedly insert the threads 166 of the extender into the implant. If the screwdriver slots are ground away during any shortening process of the extender, they can be cut back into the extender with a grinding disk. Machining tolerances of the top shaft 167 of the extender closely approximate those of the internal bore 168 of the implant. This provides lateral strength to the connection. The extender is threadedly inserted into the implant until the lip 169 of the extender seats firmly on the shoulder 170 of the bore opening 171 of the implant.

In referring to FIG. 12 there is seen a prosthetic screw 172, an extension cast-on 173, an indexing sleeve 174, and an implant 175. This configuration of components has various applications including a screw retained straight extender, a screw retained angled extender, the coping for a screw retained crown, and a screw retained coping for attachment to bars or clips for retention of removable prosthesis. The extension cast-on 173 has a sleeve of ash less plastic 176, which is affixed to a precious metal base 177. The plastic sleeve 176 can be cut, ground or altered by the addition of wax or plastic so that it can be shaped at different angles or shapes. Wax or plastic can also be flowed down onto the anatomically shaped fused abutment base 178, from the base of the extension cast-on 179 so that the changes of angle or shapes of the extension cast-on can be permanently indexed to the implant 175. This indexing results in one of two possible placements of the altered extension cast-on into the implant, 180 degrees apart. Therefore, there are only two possible insertion positions into the implant, a significant improvement over the six positions of other systems with hex indexing components. Since only one position is correct, it is easier to discern the correct insertion position when the placement is either front wards or backwards in contrast to positions that very only 60 degrees and are hard to discern. To facilitate coverage of the abutment base 178 there is provided an indexing sleeve 174, made of ash less plastic, which is affixed to the base of the extension cast-on 179 with a little luting plastic or wax. Once the extension cast-on is sufficiently altered and indexed to the implant, it is invested in investment plaster, the ash less plastic is burned out, and the void is cast with precious metal using the lost wax technique. It should be noted that the extension cast-on has features that make it rather flexible. There is a lip 180, which sits firmly on the shoulder 181 of the bore opening of the implant. If the indexing sleeve 174 is used, then the lip 180 of the extension cast-on is fused to the shoulder 182 of the sleeve. In implant sizes that are large enough, the top bore 183 of the implant may be slightly larger in diameter than the bottom shaft 184 of the prosthetic screw. In those cases an extension sheath 185 is added to the precious metal base 177. This sheath 185 engages the top bore 183 of the implant, surrounding the shaft 184 of the prosthetic screw. This feature adds strength to the connection and reduces tortional forces on the screw. The entire assembly is threadedly affixed to the implant by means of the prosthetic screw 172. This prosthetic screw has a slotted top 186 for wrench or screwdriver engagement. If the extension cast-on 173 needs to be shortened, the prosthetic screw can also be shortened. A new screwdriver slot can be readily duplicated at a lower level. The prosthetic screw has a lip 187 that seats positively onto a shoulder 188 in the extension cast-on. The component created by the lost wax casting of the extension cast-on is threadedly attached to the implant by the prosthetic screw until the lip 187 seats positively on the shoulder 188, forming a firm anti-rotational attachment.

FIG. 13 depicts an ash less plastic castable extender 189, an indexing sleeve 190, and an implant 191. The castable extender 189 may be used for cementable straight or angled abutment extenders, or may be used in the fabrication of copings for post & crown applications. The castable extender has a lip 192, which may seat positively on the shoulder 193 of the bore opening of the implant, or if the indexing sleeve 190 is used, the lip 192 is seated on the shoulder 194 of the indexing sleeve and luted in place. The castable extender 189 has a constricted neck 195 where the extender may be bent when heated so that the angle of the extender may be altered. Once the castable extender is altered by bending at the neck 195 the constriction is filled in with castable wax or plastic. The extender may also be altered in shape or length. Once the angle or concentric shape of the extender is altered, it is then indexed to the implant by use of the indexing sleeve 190 or by flowing wax down onto the non-round abutment base 196. When either the castable extender 190 or the extension cast-on 174 of FIG. 12 are incorporated into copings for crowns, the copings will generally be extended down onto the accessible portion of the parallel walls 197 of the implant, thereby establishing the margin of the crown. After the crown or extender is completed in wax and ash less plastic, it is cast with metal using the lost wax technique. This metal casting might then be further altered by the application of porcelain or attachment to other copings or bars connectors. It is then cementedly affixed to the dental implant. The top portion 198 of the extension post has close tolerances to the bore opening of the implant, while the lower portion 199 of the implant has a diameter equal to the minor diameter of the threaded bore of the implant. There are appropriate vents 200, which allow the cement to flow along side the post and out of the implant at the time of cemented fixation. This relieves hydraulic piston action and allows the component to go fully to seat when it is cementedly affixed to the implant.

It should be clear that anatomically shaped dental implants of varied sizes and generally oval, rectangular, triangular, or circular anatomic shapes have been provided, which have integrated abutment base formed thereon.

Preferentially, the anatomically shaped dental implants have the greatest diameter of the ovoid shape of the integrated abutment at or near the base of the nearly parallel walls; a position approximating the ideal positional placement of the implant relative to the crest of facial bone in anterior teeth and bicuspids. At this level, the greater dimension of the ovoid anatomic shape ideally will be equal to or greater than 3.25 mm. The minor diameter of the ovoid anatomic shape at this area may be less than 3.25 mm. Larger implants will have greater linear dimensions. Also in the posterior areas of the mouth the implants may be oriented so that the greater dimension of the anatomical shape is in the mesiodistal orientation.

The present invention also provides osteotomes, which have instrument tips that are sized and shaped like the heads of the anatomic implants, and bone rasps, which have serrated instrument tips where those instrument tips are the same size and shape of the heads of the anatomic implants. The implants integrated abutments may be coated with various aesthetic components such as ceramics, gold, or titanium nitride. Those implants with coated integrated abutments may also have the lower edge of the coatings curved coronally from the front/labial portion of the implant to the back/palatal-lingual portion of the implant so that the coatings do not come in direct contact with the bone.

Healing collars have internal anatomic openings that can be attached to correspondingly shaped and sized anatomic abutment base. These collars have extension flanges that may intentionally displace gingival tissue for ease of access to the pertinent portion of the implant during the prosthetic treatment phase. Impression transfer posts, which anatomically engage the abutment base and extend onto the parallel walls of the implant provide gingival tissue retraction during the taking of impressions of the dental implant. Extension cast-on posts and castable indexing sleeves may be united to provide copings for crowns or greater extension of the core of integrated abutment base, which are anti-rotational by virtue of their indexed relationship to the anatomically shaped dental implant.

It should be clear that the present invention is not to be limited to the forms shown which are to be considered as illustrative rather than restrictive.

The invention claimed is:

1. A method of attaching a dental implant comprising the steps of:
   extracting a tooth of a patient to create an osteotomy socket in a jawbone of the patient;
   selecting a dental implant having:
      an elongated body on a first end portion thereof for attaching to the jawbone to replace a root of the extracted tooth;
      an anatomically shaped portion above the elongated body dimensioned for fitting at least a lower section thereof into the socket, the anatomically shaped portion having two nearly parallel walls on opposed sides thereof;
      an artificial tooth abutment on a second end portion opposed to the first end portion above and integral with the anatomically shaped portion for mounting an artificial tooth thereon; and
      a bore extending axially thereinto from the abutment for attaching a post therein;
   drilling the osteotomy socket with a drill matched to a diameter and a chosen length of the implant body to thereby improve fixation of the implant to the jawbone;
   drilling the socket with a counter bevel drill to widen the socket for accepting the at least lower section of the anatomically shaped portion of the implant;
   attaching the selected dental implant into the created socket with the abutment extending above adjacent gum tissue of the patient and with a top edge of the nearly parallel walls above a crest of adjacent jawbone; and
   attaching an artificial tooth to the abutment above the adjacent jawbone crest by setting a margin of the artificial tooth along the nearly parallel walls to a position between an edge of the adjacent gum tissue and the adjacent jawbone crest.

2. A method of attaching a dental implant in accordance with claim 1 including selecting a dental implant having a coating thereon and having the abutment and at least a portion of the nearly parallel walls coated with gold.

3. A method of attaching a dental implant in accordance with claim 1 including selecting a dental implant having a coating thereon and having the abutment coated with titanium nitrite.

4. A method of attaching a dental implant in accordance with claim 1 including selecting a dental implant having a coating thereon and having the abutment coated with ceramics.

5. A method of attaching a dental implant in accordance with claim 1 including selecting a smooth anatomic osteotome of the same general shape as the anatomically shaped portion of the selected implant and placing said smooth osteotome into the osteotomy socket to determine the relationship of the implant thereto.

6. A method of attaching a dental implant in accordance with claim 5 including positioning said smooth osteotome in the osteotomy socket and hitting said osteotome with a surgical mallet to deform the osteotomy socket to more readily accept the anatomical portion of said dental implant.

7. A method of attaching a dental implant in accordance with claim 6 including selecting an anatomical rasp osteotome of the same general shape as the anatomically shaped portion of the selected implant and positioning said rasp osteotome in the osteotomy socket and hitting the rasp osteotome to deliver a blow with a surgical mallet thereby rasping the osteotomy socket to more readily accept the anatomical portion of the dental implant.

8. A method of attaching a dental implant in accordance with claim 7 including selecting a drill guide having an anatomical head of the same general shape as the anatomically shaped portion of the selected implant and inserting said drill guide into said osteotomy socket for guiding a drill to perform the drilling steps.

9. The method recited in claim 1, wherein the dental implant body has at least one of a set of grooves, threads, and fins along at least a section thereof.

10. The method recited in claim 1, wherein the elongated body is substantially cylindrical.

11. A method of attaching a dental implant comprising the steps of:
   selecting a dental implant having:
      an elongated body on a first end portion thereof for attaching to a jawbone of a patient to replace a root of an extracted tooth in an osteotomy socket;
      an anatomically shaped portion above the elongated body for fitting at least a lower section thereof into the socket, the anatomically shaped portion having two nearly parallel walls on opposed sides thereof;
      an artificial tooth abutment on a second end portion opposed to the first end portion above and integral with the anatomically shaped portion for mounting an artificial tooth thereon: and
      a bore extending axially there into from the abutment for attaching a post therein;
   enlarging the osteotomy socket to match a confirmation of the implant body to thereby improve fixation of the implant to the jawbone and to match a confirmation of the at least lower section of the anatomically shaped portion; and
   attaching the selected dental implant into the created socket with the abutment extending above adjacent gum tissue of the patient and with a top edge of the nearly parallel walls above a crest of adjacent jawbone.

12. The method recited in claim 11, wherein the dental implant body has at least one of a set of grooves, threads, and fins along at least a section thereof.

13. The method recited in claim 11, wherein the elongated body is substantially cylindrical.

* * * * *